United States Patent [19]

Bellis et al.

[11] Patent Number: 4,985,180

[45] Date of Patent: Jan. 15, 1991

[54] PROCESS FOR PREPARING PHENYL ESTERS OF SUBSTITUTED ACIDS

[75] Inventors: Harold E. Bellis; Donald J. Dumas; George C. Sonnichsen, all of Wilmington, Del.; Vinayakam Subramanyam, Boothwyn, Pa.

[73] Assignee: E. I. Du Pont de Nemours and Company, Wilmington, Del.

[21] Appl. No.: 359,981

[22] Filed: Jun. 6, 1989

Related U.S. Application Data

[63] Continuation-in-part of Ser. No. 219,644, Jul. 15, 1988, abandoned.

[51] Int. Cl.$^5$ .............. C11C 3/00; C07C 69/017
[52] U.S. Cl. .............. 260/404; 260/405; 560/17; 560/32; 560/43; 560/108; 560/109; 560/115; 560/125; 560/142; 560/145
[58] Field of Search .............. 560/108, 109, 142, 145, 560/146, 17, 32, 43, 115, 125; 260/404, 405

[56] References Cited

U.S. PATENT DOCUMENTS

| | | | |
|---|---|---|---|
| 2,659,697 | 11/1953 | Waye | 252/56 |
| 3,130,165 | 4/1964 | Brocklehurst | 252/99 |
| 3,751,453 | 8/1973 | Karkov et al. | 560/232 |
| 4,483,778 | 11/1984 | Thompson et al. | 252/94 |
| 4,536,314 | 8/1985 | Hardy et al. | 252/102 |
| 4,634,551 | 1/1987 | Burns et al. | 252/98 |
| 4,681,592 | 1/1987 | Hardy et al. | 8/111 |
| 4,778,618 | 10/1988 | Fong et al. | 252/186 |

FOREIGN PATENT DOCUMENTS

| | | |
|---|---|---|
| 0148148 | 10/1985 | European Pat. Off. |
| 0164786 | 12/1985 | European Pat. Off. |
| 0284292 | 9/1989 | European Pat. Off. |
| 1209631 | 10/1970 | United Kingdom |

OTHER PUBLICATIONS

Roczniki Chem. 41(11), 1915–1920 (1967), (Chemical Abstracts, vol. 68, 87571n (1968).
Synthesis, (1979), 295–296.
Naturforch. 346, 1737–1744, (1979).
Synthesis, (1975), 723–724.
Drewes et al; Hoppe-Seyler's Z. Physiol. Chem; Jun., 1981; pp. 745–753.

*Primary Examiner*—Werren B. Lone
*Assistant Examiner*—Vera C. Clarke
*Attorney, Agent, or Firm*—Charles E. Krukiel

[57] ABSTRACT

Phenyl esters of substituted acids are prepared by a two-step process in which a phenol derivative is first treated with an acid halide to yield a phenyl ester intermediate, and the intermediate is reacted with an appropriate nucleophile.

11 Claims, No Drawings

PROCESS FOR PREPARING PHENYL ESTERS OF SUBSTITUTED ACIDS

This application is a continuation-in-part of U.S. application Ser. No. 07/219,644 filed July 15, 1988 (now abandoned).

BACKGROUND OF THE INVENTION

The present invention relates to an improved process for preparing a broad variety of phenyl esters of the general formula (I):

$$R—ACH(R_1)CO_2Ph(CH_2)_n—R_2 \quad (I)$$

More particularly, the present invention relates to an improved two-step process for preparing phenyl esters of substituted acetic acids of formula (I), i.e., where $R_1$ is H.

The present invention also includes the discovery of novel phenyl ester intermediates of such process which can be identified by the general formula $$XCH(R_1)CO_2Ph(CH_2)_n—R_2 \quad (II)$$

as well as methods for the utilization of these intermediates as alkylating agents for amides, amines, carboxylic acids, mercaptans and phosphines.

The term "bleach activator" is understood in the art to describe a relatively stable compound which decomposes in water in the presence of a peroxygen to produce the corresponding peracid bleaching agent. The subject phenyl esters of formula (I) are useful as bleach activators or as precursors to bleach activators.

U.S. Pat. No. 4,681,592 discloses, inter alia, bleach activators of the formula:

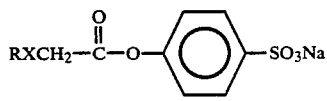

wherein R is hydrocarbyl or alkoxylated hydrocarbyl; X is, inter alia, $SO_2$, $N(R')_2$ or $P(R')_2$; and R' is H or alkyl.

European Patent Application No. 284,292 discloses, inter alia, peracid precursors of formula:

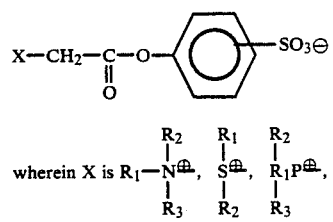

wherein X is $R_1—N^{\oplus}$, $S^{\oplus}$, $R_1P^{\oplus}$,
$\phantom{wherein X is }R_3\phantom{—N^{\oplus},}R_2\phantom{S^{\oplus},}R_3$ and $R_1$, $R_2$ and $R_3$ are, inter alia, $C_1$–$C_{30}$ alkyl.

U.S. Pat. No. 4,634,551 discloses, inter alia, bleach activators of the formula:

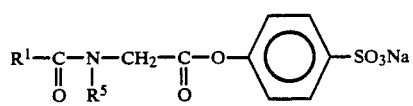

wherein $R^1$ is an alkyl(ene), aryl(ene) or alkaryl(ene) group; and $R^5$ is H or an alkyl, aryl or alkaryl group.

U.S. Pat. No. 4,778,618 discloses, inter alia, bleach activators of formula:

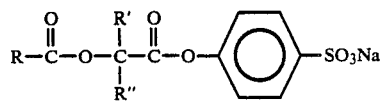

wherein R is $C_1$–$C_{20}$ linear or branched chain alkyl, alkylethoxylated, cycloalkyl, aryl, substituted aryl; R' and R" are independently H, $C_1$–$C_{20}$ alkyl, aryl, $C_1$–$C_{20}$ alkylaryl, substituted aryl, and $NR_3{}^a+$; and $R^a$ is $C_1$–$C_{30}$ alkyl.

The subject phenyl esters are conventionally prepared from the corresponding substituted acetic acids using methods which are known in the art. In most cases the substituted acetic acid can be converted to the corresponding acid chloride which is then reacted with an appropriately substituted phenol in the presence of a base or with a preformed salt of the phenol.

Known processes require three or more steps to prepare a phenyl ester of formula (I); they proceed via a substituted acetic acid; and they require the preparation of at least one acid chloride.

U.S. Pat. No. 3,130,165 discloses phenyl esters of lower ($C_2$–$C_3$) alpha-chlorocarboxylic acids as bleach activators. Among the preferred esters is chloroacetyl phenol-4-potassium sulfonate of the formula:

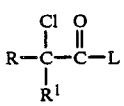

U.S. Pat. No. 3,130,165 does not disclose a method for preparing this compound.

U.S. Pat. No. 4,483,778 discloses, inter alia, bleach activators derived from higher ($C_6$–$C_{16}$) alpha-chlorocarboxylic acids of the formula

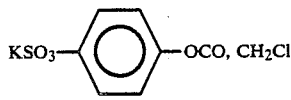

wherein R is a straight or branched alkyl or alkenyl group having from about 4 to about 14 carbon atoms, $R^1$ is H, $CH_3$, $C_2H_5$ or $C_3H_7$, and L is, inter alia, phenol sulfonate.

U.S. Pat. No. 3,130,165 and U.S. Pat. No. 4,483,778 strongly suggest that phenyl esters of formula (II) are subject to nucleophilic attack at the ester carbonyl with concomitant cleavage of the phenyl ester. (The term nucleophile is generally understood in the art to describe any reagent that brings an electron pair. The reaction of a nucleophile is termed as nucleophilic.) It has now been discovered that under certain conditions phenyl esters of formula (II) react with nucleophiles to give products resulting from displacement of the halide group X with preservation of the phenyl ester.

In addition, it has been discovered that phenyl esters of formula (II) can be simply and efficiently prepared from alpha-haloacetyl halides under a variety of conditions.

It has further been discovered that the novel compound 4-(chloroacetyloxy)benzene sulfonic acid, sodium salt, is a particularly useful intermediate for the preparation of bleach activators derived from substituted acetic acids.

SUMMARY OF THE INVENTION

The present invention is an improved two-step process for preparing phenyl esters of the general formula (I):

$$R\text{—}ACH(R_1)CO_2Ph(CH_2)_n\text{—}R_2$$

wherein

A is $CO_2(CH(R_1)CO_2)_m$, S, $N(R_4)_2^\oplus$, $P(R_5)_2^\oplus$ or $CON(R_6)$;

R is $C_1$-$C_{20}$ alkyl; alkoxylated alkyl, cycloalkyl, aryl or alkylaryl;

$R_1$ is H or $CH_3$;

$R_2$ is $SO_3M$, $OSO_3M$, $CO_2M$, or $N+(R_3)_3Q-$;

n is 0 or an integer from 1 to 4;

m is 0 or an integer from 1 to 4;

M is H, an alkali metal, an alkaline earth metal, or $N(R_3)_4{}^+$;

$R_3$ substituents are independently H or $C_1$-$C_6$ alkyl;

$R_4$ substituents are independently H or $C_1$-$C_{20}$ alkyl;

$R_5$ substituents are independently $C_1$-$C_{20}$ alkyl;

$R_6$ is H or $C_1$-$C_{10}$ alkyl, aryl or alkylaryl; and

Q is a halide with the proviso that when A is $CO_2(CH(R_1)CO_2)_m$, then $R_2$ is $SO_3M$, $OSO_3M$ or $N+(R_3)_3Q-$. Within the scope of the compounds defined by formula (I), the more commercially significant are those which are useful as bleach activators or as precursors to bleach activators and in which n is 0 or 1;

m is 0 or 1;

R is $C_6$-$C_{12}$ alkyl;

$R_1$ is H;

$R_2$ is $SO_3M$;

M is Na, K, or Mg;

$R_4$ substituents are independently H or $C_1$-$C_4$ alkyl;

$R_5$ substituents are independently $C_1$-$C_4$ alkyl $R_6$ is H or $C_1$-$C_4$ alkyl; and Q is Cl.

The process of this invention can be carried out in two distinct steps. In the first step, a phenol derivative (III) is treated with an acid halide (IV) to yield a phenyl ester intermediate of formula (II) as shown in the following Equation 1:

Equation 1:

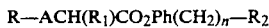

$$M_1OPh(CH_2)_n\text{—}R_2 + XCH(R_1)COY \longrightarrow$$
$$\quad\quad\quad (III) \quad\quad\quad\quad\quad (IV)$$

$$XCH(R_1)CO_2Ph(CH_2)_n\text{—}R_2 + M_1Y$$
$$\quad\quad\quad\quad (II)$$

In the second step, the intermediate (II) is reacted with an appropriate nucleophile to yield the phenyl ester (I) as shown in Equation 2a to 2e.

Equation 2:

(a)
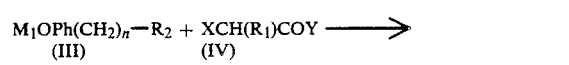
$$RCO_2(CH(R_1)CO_2)_mM_2 + II \rightarrow RCO_2(CH(R_1)\\CO_2)_{m+1}CO_2Ph(CH_2)_n\text{—}R_2 + M_2X$$

(b)
$$RSM_2 + II \rightarrow RSCH(R_1)CO_2Ph(CH_2)_n\text{—}R_2 + M_2X$$

(c)
$$RN(R_4)_2 + II \rightarrow RN^+(R_4)_2CH(R_1)CO_2Ph(CH_2)_n\text{—}R_2X^-$$

(d)
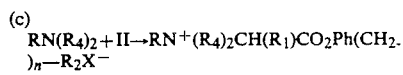
$$RP(R_4)_2 + II \rightarrow RP^+(R_4)_2CH(R_1)CO_2Ph(CH_2)_n\text{—}R_2X^-$$

(e)
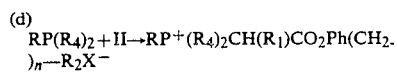
$$RCON(R_5)M_2 + II \rightarrow RCON(R_5)CH(R_1)\\CO_2Ph(CH_2)_n\text{—}R_2 + M_2X$$

wherein:

X and Y are independently Cl or Br;

A, R, $R_1$, $R_2$, $R_4$, $R_5$, n and m are as defined above; and $M_1$ and $M_2$ independently have the same meaning as M.

The present invention also includes the discovery of novel compounds of the formula (II), above, wherein:

X is Cl or Br;

$R_1$ is H or $CH_3$;

$R_2$ is $SO_3M$, $OSO_3M$ or $N+(R_3)_3Q-$;

n is zero or an integer of from 1 to 4;

M is H, an alkali metal, an alkaline earth metal, or $N(R_3)_4{}^+$;

$R_3$ substituents are independently H or $C_1$-$C_6$ alkyl; and

Q is a halide with the proviso that when $R_1$ is H n is 0 and $R_2$ is $SO_3M$ then M is not potassium. Preferred for their ease of synthesis are compounds of formula (II) wherein:

X is Cl;

n is 0 or 1;

$R_1$ is H;

$R_2$ is $SO_3M$; and

M is Na, or Mg.

More preferred for its ease of synthesis and its utility as an intermediate in preparing a bleach activator is:

4-(chloroacetyloxy)benzene sulfonic acid, sodium salt.

DETAILED DESCRIPTION OF THE INVENTION

According to the present invention, it is now possible to prepare a broad variety of phenyl esters of the following formula (I) by a substantially improved and more economical process than currently known:

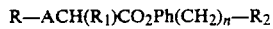

$$R\text{—}ACH(R_1)CO_2Ph(CH_2)_n\text{—}R_2 \quad\quad (I)$$

wherein

A is $CO_2(CH(R_1)CO_2)_m$, S, $N(R_4)_2^+$, $P(R_5)_2^+$ or $CON(R_6)$;

R is $C_2$-$C_{20}$ alkyl; alkoxylated alkyl, cycloalkyl, aryl or alkylaryl;

$R_1$ is H or $CH_3$;

$R_2$ is $SO_3M$, $OSO_3M$, $CO_2M$, or $N+(R_3)_3Q-$;

n is 0 or an integer from 1 to 4;

m is 0 or an integer from 1 to 4;

M is H, an alkali metal, an alkaline earth metal, or $N(R_3)_4{}^+$;

$R_3$ substituents are independently H or $C_1$-$C_6$ alkyl;

$R_4$ substituents are independently H or $C_1$-$C_{20}$ alkyl;

$R_5$ substituents are independently $C_1$-$C_{20}$ alkyl;

$R_6$ is H or $C_1$-$C_{10}$ alkyl, aryl or alkylaryl; and

Q is a halide with the proviso that when A is $CO_2(CH(R_1)CO_2)_m$, then $R_2$ is $SO_3M$, $OSO_3M$ or $N+(R_3)_3Q^-$.

Among the phenyl esters (I) which can be prepared according to the process of this invention, those derivatives wherein:

n is 0 or 1;
m is 0 or 1;
R is $C_6$–$C_{12}$ alkyl;
$R_1$ is H;
$R_2$ is $SO_3M$;
M is Na, K, or Mg;
$R_4$ substituents are independently H or methyl;
$R_5$ substituents are independently $C_1$–$C_4$ alkyl;
$R_6$ is H or $C_1$–$C_3$ alkyl; and
Q is Cl are preferred for their utility as bleach activators or precursors to bleach activators. The process of this invention is particularly useful in preparing bleach activators (I) wherein:

n is 0;
R is $C_7$–$C_9$ alkyl;
$R_2$ is $SO_3M$ and occupies the 4-position of the benzene ring; and
M is Na or K.

The term alkali metals as used herein refers to the Group 1a metals lithium, sodium, potassium, rubidium, and cesium. The term alkaline earth metals refers to the Group 2a metals beryllium, magnesium, calcium, strontium and barium. The term halide as used herein refers to fluoride, chloride, bromide, and iodide.

The phenyl esters of formula (I) are prepared by the two-step process of this invention as shown in Equations 1 and 2. In the first step, a phenol derivative (III) is treated with an acid halide (IV) to give an intermediate phenyl ester having the formula (II). In the second step, the intermediate (II) is treated with an appropriate nucleophile to give a compound of formula (I).

Equation 1

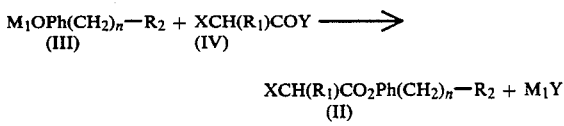

Equation 2

II + Nucleophile → I

The phenol derivatives (III) and the acid halides (IV) are known in the art or may be prepared by simple modification of methods known in the art.

The reaction according to Equation I may be carried out in an organic solvent or in the absence of a solvent. Preferably, the reaction is carried out in an aprotic solvent selected from aliphatic or aromatic hydrocarbons, halogenated aliphatic or aromatic hydrocarbons, cycloalkanes, dialkylamides, cyclic dialkylamides, ethers, cyclic ethers, polyethers, cyclic polyethers, alkylnitriles, dialkylketones, the acid halide (IV) used as starting material and mixtures thereof at temperatures between about $-20°$ and 250° C. The optimum solvent and temperature will depend on the nature of the phenol derivative (III) and the acid halide (IV) which form the starting materials. The order of addition of the starting materials is not critical; however, it is often preferable to add the acid halide (IV), or a solution of it in the reaction solvent, to a stirred mixture of the phenol derivative (III) in the reaction solvent. Although it is not essential, it is often advantageous to carry out the reaction of Equation 1 under an atmosphere of an inert gas, such as nitrogen or argon.

In cases in which the phenol derivative (III) is obtained as a hydrated material, it is beneficial to partly or fully remove the water prior to the addition of the acid halide (IV). This may be conveniently accomplished by drying in a vacuum oven or by azeotropic removal of the water in the presence of an appropriate solvent. Thus, in such cases, for best results a reaction solvent should be selected which permits the azeotropic removal of water prior to the addition of the acid halide (IV). Examples of such solvents include aliphatic and aromatic hydrocarbons, ketones, cyanoalkanes and dialkylamides, the selection of which is well within the knowledge of those skilled in the art.

The reaction of Equation 1 may be carried out using any practical ratio of the starting materials (III) and (IV). Best results are achieved, however, using a 1:1 molar ratio of reactants or an excess of the acid halide (IV), e.g., an excess of acid halide up to 1:5 or higher when no other solvents are present in the reaction.

In cases in which the phenol derivative (III) is insoluble in the reaction medium, the reaction rate may be accelerated by the addition of a phase transfer catalyst such as those described by C. M. Starks and C. Liotta in "Phase Transfer Catalysis, Principles and Techniques "(Academic Press, Inc., N.Y., N.Y., 1978), the teachings of which are incorporated herein by reference.

In some cases, the intermediate (II) will be insoluble in the reaction solvent at ambient temperature and will separate from it in pure form. Intermediates, which, because of their nature, are soluble in the reaction solvent, can be isolated by evaporation of the solvent or by precipitation from the reaction medium by the addition of a solvent in which the intermediate is of low solubility Compounds of (II) may be further purified by recrystallization or trituration with water or organic solvents or mixtures thereof. Mixtures of water and alcohols such as methanol, ethanol and isopropanol are well suited to this purpose.

When $M_1$ is H and $R_2$ is $SO_3M$, $OSO_3M$ or $CO_2M$ the reaction of Equation 1 is most conveniently carried out in aprotic solvents, such as aliphatic or aromatic hydrocarbons, halogenated aliphatic or aromatic hydrocarbons, dialkylamides or cyclic dialkylamides or mixtures thereof. The preferred reaction temperature is between 20° C. and 200° C. with temperatures below 100° C. being preferred when an amide solvent is employed and temperatures above 100° C. being preferred when a hydrocarbon solvent is employed Lower boiling hydrocarbon solvents may be employed by carrying out the reaction under sufficient pressure so as to elevate the boiling point into the desired range. In cases where the phenol (III) is insoluble in the reaction solvent, the reaction may be catalyzed by the addition of a phase transfer catalyst as discussed earlier Quaternary ammonium and quaternary phosphonium salts are particularly useful for this purpose. Although any amount of the catalyst may be employed, it is more practical to use between 0.1 and 10 mole percent relative to the phenol derivative of formula (III) with 0.5 to 5 mole percent being preferred.

Catalysts which may be used in practicing this invention include, but are not limited to, tetramethylammonium bromide, tetramethylammonium chloride, tetramethylammonium hydrogen sulfate, tetramethylammonium sulfate, tetramethylammonium iodide, tetraethylammonium bromide, tetraethylammonium chloride, tetraethylammonium hydrogen sulfate, tetraethylammonium iodide, tetrapropylammonium bromide, tetrapropylammonium chloride, tetrapropylammonium hydrogen sulfate, tetrapropylammonium iodide, methyltriethylammonium bromide, methyltriethylammonium chloride, methyltriethylammonium hydrogen sulfate, methyltriethylammonium iodide, methyltripropylammonium bromide, methyltripropylammonium chloride, methyltripropylammonium hydrogen sulfate, methyltripropylammonium iodide, methyltributylammonium bromide, methyltributylammonium chloride, methyltributylammonium hydrogen sulfate, methyltributylammonium iodide, tetrabutylammonium fluoride, tetrabutylammonium dihydrogenphosphate, tetrabutylammonium bromide, tetrabutylammonium chloride, tetrabutylammonium hydrogen sulfate, methyltrioctylammonium bromide, methyltrioctylammonium chloride, methyltrioctylammonium iodide, octadecyltrimethylammonium bromide, Aliquat® 336, hexadecyltrimethylammonium bromide, hexadecyltrimethylammonium chloride, benzyltrimethylammonium bromide, benzyltrimethylammonium chloride, benzyltriethylammonium bromide, benzyltriethylammonium chloride, benzyltributylammonium bromide, benzyltributylammonium chloride, tetrabutylphosphonium bromide, tetrabutylphosphonium chloride, hexadecyltributylphosphonium bromide, tetraphenylphosphonium bromide, tetraphenylphosphonium chloride, methyltriphenylphosphonium bromide, and methyltriphenylphosphonium iodide.

When $M_1$ is other than H, the reaction of Equation 1 is carried out in an inert aprotic solvent such as, for example, dimethylformamide, dimethylacetamide, 1-methyl-2-pyrrolidinone, tetrahydrofuran, acetonitrile, toluene, xylenes or glymes. Compounds of formula (III) where $M_1$ is other than H may be prepared by treating compounds of formula (III) where $M_1$ is H with an appropriate base, i.e., the corresponding metal hydroxide, metal carbonate, metal bicarbonate, metal hydride, metal alkoxide or an amine. The intermediates (III) where $M_1$ is other than H can be generated in a discrete reaction step and isolated prior to use or they may be generated in situ by combining the base with the phenol derivative (III) and the acid halide (IV) in the presence of the reaction solvent. The optimum order for the addition of the reagents will vary from case to case; however, good results can be achieved by adding the base to a mixture of the phenol derivative (III) (wherein $M_1$ is H) in the reaction solvent and then adding the acid halide (IV) to the resulting mixture.

The reaction of Equation 2 is best carried out in an aprotic organic solvent or in mixtures of aprotic organic solvents at temperatures between $-20°$ and $200°$ C. with temperatures between $0°$ and $150°$ C. being preferred and temperatures between $20°$ and $100°$ being most preferred. The optimum solvent and temperature will depend on the nature of the ester intermediate (II) and the nucleophile which comprise the starting materials. Typical solvents include dimethylsulfoxide, dimethylformamide, dimethylacetamide, 1-methyl-2-pyrrolidinone, acetonitrile, tetrahydrofuran, acetone, methylethylketone, toluene, xylenes and mixtures thereof. In some cases, it may be more convenient to carry out the reaction in the absence of a solvent. Polar aprotic solvents such as dimethylsulfoxide, dimethylformamide, dimethylacetamide and 1-methyl-2-pyrrolidinone are preferred with the amide solvents being most preferred. The optimum order of addition of the reagents will vary from case to case; however, it is often convenient to first combine the intermediates (II) and the solvent and then add the nucleophile Although not essential, it is often advantageous to carry out the reaction under an inert gas, such as nitrogen or argon.

The reaction of Equation 2 may be carried out using any practical ratio of compound (II) and the nucleophile. In most cases, a 1:1 molar ratio of reactants is satisfactory, or an excess of up to 10% of the nucleophile may be used.

In cases in which either or both of the starting materials are insoluble in the reaction medium, the process may be accelerated by the addition of a phase transfer catalyst as discussed earlier for the reaction of Equation 1. Although any amount of catalyst may be employed, it is more practical to use between 0.5 and 100 mole percent relative to the intermediate of formula (II).

In some cases the product esters (I) will be insoluble in the reaction medium at ambient temperature, and will separate from it in pure form. Esters (I) which are soluble in the reaction solvent can be isolated by evaporating the solvent or by precipitating the ester from the reaction medium by adding a solvent in which the ester (I) is of low solubility. Solvents such as acetonitrile, tetrahydrofuran, acetone, aliphatic hydrocarbons and aromatic hydrocarbons are particularly useful for this purpose. The esters (I) may be further purified by recrystallization or trituration with water or organic solvents or mixtures thereof. Mixtures of water and alcohols such as methanol, ethanol and isopropanol are often well suited to this purpose.

Salts of carboxylic acids, mercaptans and amides may be prepared by treatment of the corresponding carboxylic acid, mercaptan or amide with an appropriate base, i.e., the corresponding metal hydroxide, metal carbonate, metal bicarbonate, metal hydride, metal alkoxide or an amine These salts can be generated in a discreet reaction step and isolated prior to use or they may be generated in situ by combining the base, the carboxylic acid, mercaptan or amide and the phenyl ester (II) in the presence of the reaction solvent The optimum order for the addition of the reagents will vary from case to case; however, good results can be achieved by adding the acid, mercaptan or amide to a mixture of the base and the phenyl ester (II) in the reaction solvent.

It will be appreciated by those skilled in the art that compounds of formula (I) and formula (II) wherein M is H may be converted to the corresponding salts by treatment with an appropriate base It will also be appreciated by those skilled in the art that when two or three of the substituents M, $M_1$ and $M_2$ are other than H it will be advantageous to use salts with the same counterion so that a product incorporating a single counterion is obtained.

It will also be appreciated by those skilled in the art that compounds of formula (I) wherein A is S can be converted to the corresponding sulfoxides and sulfones using methods which are will known in the art.

In a further embodiment of this invention, the two-step process may be carried out in a single reactor. This may be accomplished by either exchanging the solvents between steps or by selecting a solvent which is suitable for both steps.

EXAMPLE 1

Preparation of 4-(chloroacetyloxy)benzene sulfonic acid, sodium salt.

A slurry of 69.6 g (0.30 mole) of 4-hydroxybenzenesulfonic acid, sodium salt dihydrate, and 600 mL of mixed xylenes was heated to reflux for four hours with azeotropic removal of a total of 100 mL of xylenes and water using a Dean-Stark trap. The mixture was allowed to cool to 60° C. and 2.04 g (0.006 mole) of tetra-n-butylphosphonium chloride was added followed by 26.8 mL (0.33 mole) of chloroacetyl chloride. The mixture was heated to reflux for six hours and then allowed to cool to room temperature. The white solid product was collected by filtration, washed with 100 mL of toluene and dried at 50° to 60° C. under reduced pressure to give 80.1 g of product $^1$H NMR (DMSO-$d_6$, 300 MHz) indicated a 50:1 mixture of 4-(chloroacetyloxy)-benzenesulfonic acid, sodium salt, and 4-hydroxybenzenesulfonic acid, sodium salt: $\delta$4.71 (s, 2 H, CO$_2$CH$_2$Cl), 7.14 (d, 2 H, J=8.8 Hz), 7.68 (d, 2 H, J=8.8 Hz).

EXAMPLE 2

Preparation of 4-(nonanoyloxyacetyloxy)benzene sulfonic acid, sodium salt.

A slurry of 9.0 g (0.05 mole) of nonanoic acid, sodium salt, 13.7 g (0.05 mole) of 4-(chloroacetyloxy)benzenesulfonic acid, sodium salt, and 100 mL of dimethylformamide was heated with mechanical stirring at 35°–40° C. for three hours and then at 50° C. for three hours The mixture was allowed to cool and stirring continued at ambient temperature for an additional 16 hours. The solvent was then removed under reduced pressure and the residue recrystallized from 2:1 isopropanol:water to give 13.3 g of off white flakes $^1$H NMR (DMSO-$d_6$, 300 MHz) $\delta$0.85 (t, 3 H), 1.25 (multiplet, 10 H), 1.58 (quintet, 2 H), 2.43 (t, 2 H), 4.95 (s, 2 H, CO$_2$CH$_2$CO$_2$), 7.10 (d, 2 H), 7.67 (d, 2 H).

EXAMPLE 3

One pot preparation of 4-(nonanoyloxyacetyloxy)benzenesulfonic acid, sodium salt.

To a mechanically stirred suspension of 275 g (1.26 mole) of 4-hydroxybenzenesulfonic acid, disodium salt, in 1.2 L of dimethylformamide was added dropwise over 15 minutes 146.6 g (1.3 mole) of chloroacetyl chloride. The mixture, which had warmed to 67° C. during the addition, was stirred for an additional two hours during which time the temperature dropped to 35° C. To this was then added 236 g (1.3 mole) of sodium nonanoate and the mixture was heated at 50° C. for six hours. The mixture was then refrigerated for 16 hours and the solids separated by filtration. The filter cake was recrystallized from 250 mL of 7:3 isopropanol:water to give 127 g of product. $^1$H NMR (DMSO-$d_6$, 300 MHz) analysis of this material indicated that it was an 11:1 molar mixture of 4-(nonanoyloxyacetyloxy)benzenesulfonic acid, sodium salt, and 4-hydroxybenzenesulfonic acid, sodium salt. The dimethylformamide filtrates were concentrated under reduced pressure and the residue recrystallized from 7:3 isopropanol:water to give an additional 115 g of product. $^1$H NMR analysis of this material indicated that it was an 4:1 molar mixture of (4-nonanoyloxyacetyloxy)benzenesulfonic acid, sodium salt, and 4-hydroxybenzenesulfonic acid, sodium salt.

EXAMPLE 4

Preparation of 4-(nonanoyloxyacetyloxyacetyloxy)benzene sulfonic acid, sodium salt.

A stirrer slurry of 21.6 g (0.10 mole) of nonanoyloxyacetic acid, 24.8 g (0.091 mole) of 4-(chloroacetyloxy)-benzene sulfonic acid, sodium salt, 10.6 g (0.10 mold) of powdered sodium carbonate and 500 mL of dimethylacetamide was heated at 55° C. for 6 hours. The reaction mixture was then filtered hot and the solids washed with 150 mL of hot (55° C.) dimethylacetamide. The filtrate was then diluted with 650 mL of acetonitrile and the resulting slurry refrigerated at 0° C. for 40 hours. The precipitated product was collected, washed with acetonitrile and dried at 50° C. to 60° C. under reduced pressure to give 17.17 g of product. $^1$H NMR (DMSO-$d_6$, 300 MHz) $\delta$0.85 (t, 3H), 1.25 (m, 10H), 1.55 (quintet, 2H), 2.40 (t,2H), 4.83 (s, 2H), 5.05 (s, 2H), 7.10 (d, 2H), 7.67 (d, 2H).

EXAMPLE 5

Preparation of 4-(dimethyloctylaminoacetoxy) benzene sulfonic acid.

To a stirred slurry of 54.5 g (0.2 mole) of 4-(chloroacetyloxy)benzene sulfonic acid, a sodium salt, in 250 mL of dimethylacetamide was added dropwise over 15 minutes 31.5 g (0.2 mole) of dimethyloctylamine. After stirring for an additional 3 hours, the contents of the flask became a solid mass. This was slurried with 200 mL of acetone, filtered, washed twice with 250 mL potions of acetone and dried at 50°-60° C. under reduced pressure to give 74 g of product. $^1$H NMR (DMSO-$d_6$) $\delta$0.9 (t, 3H), 1.24 (m, 10H), 1.6 (m, 2H), 3.3 (s, 6H), 3.5 (m 2H), 4.95 (s, 2H), 7.1 (d, 2H), 7.7 (d, 2H).

The present invention also includes novel intermediates which are obtained in step one of the above-described process and have the formula (II):

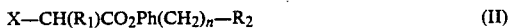

$$X-CH(R_1)CO_2Ph(CH_2)_n-R_2 \qquad (II)$$

wherein:
X is Cl or Br;
$R_1$ is H or CH$_3$;
$R_2$ is SO$_3$M, OSO$_3$M or N+(R$_3$)$_3$Q−;
n is 0 or an integer from 1 to 4;
M is H, an alkali metal an alkaline earth metal, N(R$_3$)$_4$+;
$R_3$ substituents are independently H or C$_1$-C$_6$ alkyl; and
Q is halide,
with the proviso that when $R_1$ is H, n is 0 and $R_2$ is SO$_3$M, then M is not potassium. Preferred among the foregoing intermediates (II) are those wherein:
X is Cl;
n is 0 or 1;
$R_1$ is H;
$R_2$ is SO$_3$M; and
M is Na or Mg.
Most preferred among the foregoing intermediates (II) is: 4-(chloroacetyloxy)benzene sulfonic acid, sodium salt.

It will be appreciated by those skilled in the art that the process of this invention is not specifically limited to the preparation of the compounds defined by formula (I). Contemplated equivalents are those cases in which the groups R, $R_1$, $R_4$, $R_5$ and $R_6$ are independently optionally substituted alkyl, cycloalkyl, aryl or alkoxyaryl provided that the substituents do not contain functional groups which would interfere with the process. In the same way the phenyl ester group may be fully substituted so long as the substituted group does not interfere with the process.

The compounds defined by formula (I) are useful as bleach activators, i.e., they can be formulated with other ingredients into a bleaching composition. Such bleaching compositions are formulated to provide efficient bleaching of textiles over a wide range of washing temperatures. Bleach activators of the type which can be prepared according to the process of the invention are also referred to as bleach precursors or laundry detergent additives, and bleaching compositions containing such additives can be prepared as described in the patents cited hereinabove, the teachings of which are incorporated herein by reference.

We claim:

1. A process for preparing a compound of the formula:

$$R-ACH(R_1)CO_2Ph(CH_2)_n-R_2$$

wherein

A is $CO_2(CH(R_1)CO_2)_m$, S, $N(R_4)_2^+$, $P(R_5)_2^+$ or $CON(R_6)$;
R is $C_1-C_{20}$ alkyl; alkoxylated alkyl, cycloalkyl, aryl or alkylaryl;
$R_1$ is H or $CH_3$;
$R_2$ is $SO_3M$, $OSO_3M$, $CO_2M$, or $N+(R_3)_3Q-$;
n is 0 or an integer from 1 to 4;
m is 0 or an integer from 1 to 4;
M is H, an alkali metal, an alkaline earth metal, or $N(R_3)_4^+$;
$R_3$ substituents are independently H or $C_1-C_6$ alkyl;
$R_4$ substituents are independently H or $C_1-C_{20}$ alkyl;
$R_5$ substituents are independently $C_1-C_{20}$ alkyl;
$R_6$ is H or $C_1-C_{10}$ alkyl, aryl or alkylaryl; and
Q is a halide with the proviso that when A is $CO_2(CH(R)CO_2)$ then $R_2$ is $SO_3M$, $OSO_3M$ or $N+(R_3)_3Q-$; which comprises, in a first step, treating a phenol derivative of the formula:

$$M_1-OPh(CH_2)_n-R_2$$

with an acid halide of the formula:

$$X-CH(R_1)CO-Y$$

in the optional presence of a solvent and optional presence of a phase transfer catalyst to yield a phenyl ester intermediate of the formula:

$$X-CH(R_1)CO_2Ph(CH_2)_n-R_2$$

and, in a second step, reacting the intermediate in the optional presence of a solvent with a nucleophile of the formula:

$RCO_2(CH(R_1)CO_2)_mM_2$, $RSM_2$, $RN(R_2)_2$, $RP(R_4)_2$ or $RCON(R_5)M_2$ wherein X and Y are independently Cl or Br; and
$M_1$ and $M_2$ independently have the same meaning as M.

2. The process of claim 1 wherein the phenol derivative is treated with the acid halide in the presence of an aprotic solvent selected from the group consisting of aliphatic or aromatic hydrocarbons, halogenated aliphatic or aromatic hydrocarbons, cycloalkanes, dialkylamides, cyclic dialkylamides, ethers, cyclic ethers, polyethers, cyclic polyethers, alkylnitriles, dialkylketones and excess acid halide and mixtures thereof.

3. The process of claim 2 wherein the phenol derivative is treated with the acid halide under an atmosphere of argon or nitrogen.

4. The process of claim 2 wherein the phenol derivative is insoluble in the solvent and the treatment of the phenol derivative with the acid halide is catalyzed by 0.1 to 10 mole percent of a phase transfer catalyst selected from the group consisting of quaternary ammonium and quaternary phosphonium salts.

5. The process of claim 4 wherein $M_1$ is H and the solvent is an aliphatic or aromatic hydrocarbon or halogenated aliphatic or aromatic hydrocarbon or excess acid halide or mixtures thereof.

6. The process of claim 2 wherein the solvent is selected from the group consisting of dimethylformamide, dimethylactamide, 1-methyl-2-pyrrolidinone, tetrahydrofuran, acetonitrile, toluene, xylenes, and glymes.

7. The process of claim 1, claim 2, or claim wherein the intermediate is reacted with a nucleophile in an aprotic organic solvent at a temperature of from 0° C. to 200° C.

8. The process of claim 7 wherein the solvent is selected from the group consisting of dimethylsulfoxide, dimethylformamide, dimethylacetamide, 1-methyl-2-pyrrolidinone, acetonitrile, tetrahydrofuran, acetone, methylethylketone, toluene, and xylenes.

9. A compound of the formula $$X-CH(R_1)CO_2Ph(CH_2)_n-R_2$$

wherein

X is Cl or Br;
$R_1$ is H or $CH_3$;
$R_2$ is $SO_3M$, $OSO_3M$ or $N+(R_3)_3Q-$;
n is 0 or an integer from 1 to 4;
M is H, an alkali metal, an alkaline earth metal $N(R_3)_4+$;
$R_3$ substituents are independently H, or $C_1-C_{16}$ alkyl; and
Q is a halide with the proviso that when $R_1$ is H, n is 0 and $R_2$ is $SO_3M$, then M is not potassium.

10. A compound of claim 9 wherein
X is Cl;
n is 0 or 1;
$R_1$ is H;
$R_2$ is $SO_3M$; and
M is Na, or Mg.

11. The compound of claim 10 which is 4-(chloroacetyloxy)benzenesulfonic acid, sodium salt.

* * * * *